United States Patent
Schindler et al.

(10) Patent No.: US 7,087,802 B2
(45) Date of Patent: Aug. 8, 2006

(54) METHOD FOR THE DEHYDROGENATION OF HYDROCARBONS

(75) Inventors: Goetz-Peter Schindler, Mannheim (DE); Otto Machhammer, Mannheim (DE); Klaus Harth, Altleiningen (DE); Klaus Joachim Müller-Engel, Stutensee (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 314 days.

(21) Appl. No.: 10/380,552

(22) PCT Filed: Sep. 14, 2001

(86) PCT No.: PCT/EP01/10673

§ 371 (c)(1),
(2), (4) Date: Mar. 17, 2003

(87) PCT Pub. No.: WO02/26668

PCT Pub. Date: Apr. 4, 2002

(65) Prior Publication Data

US 2004/0030214 A1 Feb. 12, 2004

(30) Foreign Application Priority Data

Sep. 26, 2000 (DE) .......................... 100 47 642

(51) Int. Cl.
*C07C 5/327* (2006.01)

(52) U.S. Cl. ..................... 585/660; 585/654; 585/661; 585/663; 585/659

(58) Field of Classification Search ................ 585/654, 585/659, 660, 661, 663
See application file for complete search history.

(56) References Cited

U.S. PATENT DOCUMENTS

| 4,171,779 | A | * | 10/1979 | Kamp | 242/473.6 |
| 4,376,225 | A | * | 3/1983 | Vora | 585/659 |
| 4,788,371 | A | | 11/1988 | Imai et al. | 585/660 |
| 4,886,928 | A | | 12/1989 | Imai et al. | 585/660 |
| 5,633,421 | A | | 5/1997 | Iezzi et al. | 585/660 |
| 5,733,518 | A | | 3/1998 | Durante et al. | 423/248 |

FOREIGN PATENT DOCUMENTS

| EP | 838 534 | 4/1998 |
| EP | 1 074 299 | 2/2001 |
| WO | 94/29021 | 12/1994 |
| WO | 96/33150 | 10/1996 |
| WO | 96/33151 | 10/1996 |

OTHER PUBLICATIONS

Derwent Abst 2001–292595/31.

* cited by examiner

*Primary Examiner*—Tam Nguyen
(74) *Attorney, Agent, or Firm*—Novak Druce & Quigg; Daniel S. Kim

(57) ABSTRACT

In a process for the heterogeneously catalyzed dehydrogenation in one or more reaction zones of one or more dehydrogenatable $C_2$–$C_{30}$-hydrocarbons in a reaction gas mixture comprising them, with at least part of the heat of dehydrogenation required being generated directly in the reaction gas mixture in at least one reaction zone by combustion of hydrogen, the hydrocarbon or hydrocarbons and/or carbon in the presence of an oxygen-containing gas, the reaction gas mixture comprising the dehydrogenatable hydrocarbon or hydrocarbons is brought into contact with a Lewis-acid dehydrogenation catalyst which has essentially no Brönsted acidity.

18 Claims, No Drawings

METHOD FOR THE DEHYDROGENATION OF HYDROCARBONS

The present invention relates to a process for the heterogeneously catalyzed dehydrogenation of dehydrogenatable $C_2$–$C_{30}$-hydrocarbons.

Dehydrogenated hydrocarbons are required in large quantities as starting materials for numerous industrial processes. For example, dehydrogenated hydrocarbons are used in the production of detergents, antiknock gasoline and pharmaceutical products. Likewise, numerous plastics are produced by polymerization of olefins.

For example, acrylonitrile, acrylic acid or $C_4$ oxo alcohols are prepared from propylene. Propylene is at present produced predominantly by steam cracking or catalytic cracking of suitable hydrocarbons or hydrocarbon mixtures such as naphtha.

Propylene can also be prepared by heterogeneously catalyzed dehydrogenation of propane.

To obtain acceptable conversions in heterogeneously catalyzed dehydrogenations even on a single pass through the reactor, relatively high reaction temperatures generally have to be employed. Typical reaction temperatures for gas-phase dehydrogenations are from 300 to 700° C. In general, one molecule of hydrogen is produced per molecule of hydrocarbon.

The dehydrogenation of hydrocarbons proceeds endothermically. The heat of dehydrogenation necessary for obtaining a desired conversion has to be introduced into the reaction gas either beforehand and/or during the course of the catalytic dehydrogenation. In most known dehydrogenation processes, the heat of dehydrogenation is generated outside the reactor and is introduced into the reaction gas from the outside. However, this requires complicated reactor and process concepts and leads, particularly at high conversions, to steep temperature gradients in the reactor, which is accompanied by the risk of increased byproduct formation. Thus, for example, a plurality of adiabatic catalyst beds can be arranged in annular gap reactors connected in series. The reaction gas mixture is superheated by means of heat exchangers on its way from one catalyst bed to the next catalyst bed and cools down again during passage through the subsequent reactor. To achieve high conversions using such a reactor concept, it is necessary either to increase the number of reactors connected in series or to increase the reactor inlet temperature of the gas mixture. The resulting superheating inevitably leads to increased byproduct formation due to cracking reactions. Another known method is to arrange the catalyst bed in a tube reactor and to generate the heat of dehydrogenation by burning combustible gases outside the tube reactor and introduce it into the interior of the reactor via the tube wall. In these reactors, high conversions lead to steep temperature gradients between the wall and the interior of the reation tube.

An alternative is to generate the heat of dehydrogenation directly in the reaction gas mixture of the dehydrogenation by oxidation of hydrogen formed in the dehydrogenation or additionally fed in or of hydrocarbons present in the reaction gas mixture by means of oxygen. For this purpose, an oxygen-containing gas and possibly hydrogen is/are added to the reaction gas mixture either upstream of the first catalyst bed or upstream of subsequent catalyst beds. The heat of reaction liberated in the oxidation also prevents high temperature gradients in the reactor at high conversions. At the same time, a very simple process concept is realized by omission of the indirect heating of the reactor.

U.S. Pat. No. 4,788,371 describes a process for steam dehydrogenation of dehydrogenatable hydrocarbons in the gas phase combined with oxidative reheating of the intermediates, with the same catalyst being used for the selective oxidation of hydrogen and the steam dehydrogenation. Here, hydrogen can be introduced as co-feed. The catalyst used comprises a noble metal of group VIII, an alkali metal and a further metal selected from the group consisting of B, Ga, In, Ge, Sn and Pb on an inorganic oxide support such as aluminum oxide. The process can be carried out in one or more stages in a fixed or moving bed.

WO 94/29021 describes a catalyst which comprises a support consisting essentially of a mixed oxide of magnesium and aluminum Mg(Al)O and also a noble metal of group VIII, preferably platinum, a metal of group IVA, preferably tin, and possibly an alkali metal, preferably cesium. The catalyst is used in the dehydrogenation of hydrocarbons, which can be carried out in the presence of oxygen.

U.S. Pat. No. 5,733,518 describes a process for the selective oxidation of hydrogen by oxygen in the presence of hydrocarbons such as n-butane over a catalyst comprising a phosphate of germanium, tin, lead, arsenic, antimony or bismuth, preferably tin. The combustion of the hydrogen generates, in at least one reaction zone, the heat of reaction necessary for the endothermic dehydrogenation.

EP-A 0 838 534 describes a catalyst for the steam-free hydrogenation of alkanes, in particular isobutane, in the presence of oxygen. The catalyst used comprises a platinum group metal applied to a support comprising tin oxide/zirconium oxide and having a tin content of at least 10%. The oxygen content of the feed stream for the dehydrogenation is calculated so that the quantity of heat generated by the combustion reaction of hydrogen and oxygen is equal to the quantity of heat required for the dehydrogenation.

WO 96/33151 describes a process for the dehydrogenation of a $C_2$–$C_5$-alkane in the absence of oxygen over a dehydrogenation catalyst comprising Cr, Mo, Ga, Zn or a group VIII metal with simultaneous oxidation of the resulting hydrogen over a reducible metal oxide, e.g. an oxide of Bi, In, Sb, Zn, Tl, Pb or Te. The dehydrogenation has to be interrupted at regular intervals in order to reoxidize the reduced oxide by means of an oxygen source. U.S. Pat. No. 5,430,209 describes a corresponding process in which the dehydrogenation step and the oxidation step proceed sequentially and the associated catalysts are separated physically from one another. Catalsyts used for the selective oxidation of hydrogen are oxides of Bi, Sb and Te and also their mixed oxides.

Finally, WO 96/33150 describes a process in which a $C_2$–$C_5$-alkane is dehydrogenated over a dehydrogenation catalyst in a first stage, the output gas from the dehydrogenation stage is mixed with oxygen and, in a second stage, passed over an oxidation catalyst, preferably $Bi_2O_3$, so as to selectively oxidize the hydrogen formed to water, and, in a third stage, the output gas from the second stage is again passed over a dehydrogenation catalyst.

The catalyst system used has to meet demanding requirements in respect of achievable alkane conversion, selectivity to formation of alkenes, mechanical stability, thermal stability, carbonization behavior, deactivation behavior, regenerability, stability in the presence of oxygen and insensitivity to catalyst poisons such as CO, sulfur- and chlorine-containing compounds, alkynes, etc., and economics.

The catalysts of the prior art do not meet these requirements, particularly in respect of the achievable conversions and selectivities, operating lives and regenerability, to a satisfactory extent.

It is an object of the present invention to provide a process for the dehydrogenation of hydrocarbons which ensures high conversions, space-time yields and selectivities.

We have found that this object is achieved by a process for the heterogeneously catalyzed dehydrogenation in one or more reaction zones of one or more dehydrogenatable $C_2$–$C_{30}$-hydrocarbons in a reaction gas mixture comprising them, with at least part of the heat of dehydrogenation required being generated directly in the reaction gas mixture in at least one reaction zone by combustion of hydrogen, the hydrocarbon or hydrocarbons and/or carbon in the presence of an oxygen-containing gas, wherein the reaction gas mixture comprising the dehydrogenatable hydrocarbon or hydrocarbons is brought into contact with a Lewis-acid dehydrogenation catalyst which has essentially no Brönsted acidity.

The dehydrogenation catalyst used according to the present invention has essentially no Brönsted acidity, but a high Lewis acidity. The determination of the Lewis and Brönsted acidities of the dehydrogenation catalysts is carried out by adsorption of pyridine as basic probe molecule on the activated catalyst with subsequent quantitative FT-IR-spectrometric determination of the Brönsted- and Lewis-specific adsorbates. This method makes use of the fact that the adsorbed probe molecules give different IR spectra depending on whether they are bound to a Brönsted center or a Lewis center. At the Brönsted center, proton transfer takes place to form a local ion pair with the pyridinium ion as cation. The adsorbed pyridinium ion displays a Brönsted-specific absorption band at 1545 $cm^{-1}$ in the IR spectrum. At the Lewis center, on the other hand, the probe molecule pyridine is coordinated via its free electron pair on the ring nitrogen to the electron-deficient center. This results in an IR spectrum different to that of the Brönsted adsorbate. The Lewis band is found at 1440 $cm^{-1}$. Quantitative evaluation of the Brönsted and Lewis bands enables the Brönsted and Lewis centers to be determined separately. The band assignment is based on the work of Turkevich (C. H. Kline, J. Turkevich: J. Chem. Phys. 12, 300 (1994)).

The assignment of the resulting pyridine bands in the FT-IR spectrum is as follows:
Lewis (L): 1440 $cm^{-1}$
Brönsted (B): 1545 $cm^{-1}$
Control band B+L: 1490 $cm^{-1}$
Physisorbed pyridine: 1590 $cm^{-1}$ (additionally 1440 $cm^{-1}$)

The transmission cell used for the measurements is a reconstruction of the prototype of Gallei and Schadow (E. Gallei et al.: Rev. Sci. Instrur. 45 (12), 1504 (1976)). The cell comprises a stainless steel body with parallel IR-transparent windows made of $CaF_2$. The intrinsic absorption of the windows makes it possible to measure only in a spectral range of about 1200–4000 $cm^{-1}$. A circuit for cooling or heating fluid is provided in the cell body. In the lid of the cell there is a solid, plate-shaped sample holder with built-in cartridge heating (400° C.). The self-supporting sample compound is laid in an annular double template and screwed into the heating plate, and the cell lid is screwed onto the cell body. The measurement cell can be evacuated to $10^{-5}$–$10^{-6}$ mbar.

For sample preparation, the catalyst material is ground finely in a mortar and pressed between two stainless steel plates with mica underlays in a film press at a pressing pressure of 50 kN to give a self-supporting wafer. The thickness depends on the intrinsic IR absorption of the material and is typically in the range from 30 to 100 μm. Pellets having a diameter of about 5 mm are cut from the wafer.

The activation of the sample in the measurement cell is carried out in air at 390° C. After heating, the cell is evacuated to $10^{-5}$–$10^{-6}$ mbar. It is then cooled to the gas treatment temperature of 80° C. under a high vacuum.

The sample is subsequently treated with gaseous pyridine at a pressure which can be from $10^{-2}$ to 3 mbar. Control spectra of the sample with adsorbate are recorded until a steady adsorption state has been established at the gas treatment pressure concerned. The cell is subsequently evacuated to a high vacuum ($10^{-5}$ mbar). This removes physisorbates. After evacuation is complete, adsorbate spectra are recorded.

To determine the Lewis and Brönsted acidities, the intensities of the bands at 1440 $cm^{-1}$ and 1545 $cm^{-1}$ obtained at a particular thickness of the sample and a set equilibrium pressure of pyridine are evaluated in comparison with one another. If no band at 1545 $cm^{-1}$ is discernible (no Brönsted acidity), the band at 1490 $cm^{-1}$ can also be employed for determining the Lewis acidity.

The measured absorbances are expressed as a ratio to the thickness of the sample (in integrated extinction units (IEE) per μm of thickness). The single-beam spectrum of the sample which has not been treated with pyridine gas (cooled to 80° C.) under high vacuum serves as background of the adsorbate spectra. This completely balances out matrix bands.

1 AU corresponds to one thousand times the measured absorbance (reported in integrated extinction units IEE) divided by the thickness of the sample (in μm) obtained in the determination of the Lewis and Brönsted acidities of the dehydrogenation catalysts using the probe gas pyridine.

The dehydrogenation catalysts used according to the present invention generally have no detectable Brönsted acidity, i.e. their Brönsted acidity is less than 0.1 AU. However, they have a high Lewis acidity. The Lewis acidity of the dehydrogenation catalysts is generally greater than 1 AU, preferably greater than 3 AU, particularly preferably greater than 6 AU.

The dehydrogenation catalysts used according to the present invention generally comprise a support and an active composition. The support comprises a heat-resistant oxide or mixed oxide. The dehydrogenation catalyst preferably comprises a metal oxide selected from the group consisting of zirconium dioxide, zinc oxide, aluminum oxide, silicon dioxide, titanium dioxide, magnesium oxide, lanthanum oxide, cerium oxide and mixtures thereof as support. Preferred supports are zirconium dioxide and/or silicon dioxide; particular preference is given to mixtures of zirconium dioxide and silicon dioxide.

The active composition of the dehydrogenation catalyst used according to the present invention generally comprises one or more elements of transition group VIII, preferably platinum and/or palladium, particularly preferably platinum. In addition, the dehydrogenation catalyst can further comprise one or more elements of main groups I and/or II, preferably potassium and/or cesium. The dehydrogenation catalyst may also further comprise one or more elements of transition group III including the lanthanides and actinides, preferably lanthanum and/or cerium. Finally, the dehydrogenation catalyst can further comprise one or more elements of main groups III and/or IV, preferably one or more elements selected from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

To produce the dehydrogenation catalysts used according to the present invention, it is possible to use precursors of oxides of zirconium, silicon, aluminum, titanium, magnesium, lanthanum or cerium which can be converted into the oxides by calcination. These can be produced by known methods, for example by the sol-gel process, precipitation of salts, dehydration of the corresponding acids, dry mixing, slurrying or spray drying. For example, to produce a $ZrO_2.Al_2O_3.SiO_2$ mixed oxide, a water-rich zirconium oxide of the formula $ZrO_2.xH_2O$ can firstly be prepared by precipitation of a suitable zirconium-containing precursor. Suitable precursors of zirconium are, for example, $Zr(NO_3)_4$, $ZrOCl_2$ or $ZrC_4$. The precipitation itself is carried out by addition of a base such as NaOH, KOH, $Na_2CO_3$ or $NH_3$ and is described, for example, in EP-A 0 849 224.

To produce a $ZrO_2.SiO_2$ mixed oxide, the zirconium-containing precursor obtained above can be mixed with a silicon-containing precursor. Well-suited precursors of $SiO_2$ are, for example, water-containing sols of $SiO_2$ such as Ludox™. The two components can be mixed, for example, by simple mechanical mixing or by spray drying in a spray dryer.

To produce a $ZrO_2.SiO_2.Al_2O_3$ mixed oxide, the $SiO_2.ZrO_2$ powder mixture obtained as described above can be admixed with an aluminum-containing precursor. This can be achieved, for example, by simple mechanical mixing in a kneader. However, the $ZrO_2.SiO_2.Al_2O_3$ mixed oxide can also be produced in a single step by dry mixing the individual precursors.

The supports for the dehydrogenation catalysts used according to the present invention have, inter alia, the advantage that they can easily be shaped. For this purpose, the powder mixture obtained is admixed with a concentrated acid in a kneader and then converted into a shaped body, e.g. by means of a ram extruder or a screw extruder.

The dehydrogenation catalysts used according to the present invention have, in particular embodiments, a defined pore structure. When using mixed oxides, it is possible to influence the pore structure in a targeted manner. The particle sizes of the various precursors influence the pore structure. Thus, for example, macropores can be generated in the microstructure by use of $Al_2O_3$ having a low loss on ignition and a defined particle size distribution. In this context, the use of $Al_2O_3$ having a loss on ignition of about 3% (e.g. Puralox®) has been found to be useful.

A further possible way of producing supports having specific pore radius distributions for the dehydrogenation catalysts used according to the present invention is to add various polymers during production of the support and subsequently to remove them completely or partly by calcination so as to form pores in defined pore ranges. Mixing the polymers and the oxide precursors can be carried out, for example, by simple mechanical mixing or by spray drying in a spray dryer.

The use of PVP (polyvinylpyrrolidone) has been found to be particularly useful for producing supports having a bimodal pore radius distribution. If PVP is added to one or more oxide precursors of oxides of the elements Zr, Ti, Al or Si in a production step, macropores having sizes in the range from 200 to 5000 nm are formed after calcination. A further advantage of the use of PVP is that it makes the support easier to shape. Thus, extrudates having good mechanical properties can readily be produced from freshly precipitated hydrous $ZrO_2.xH_2O$ which has previously been dried at 120° C. when PVP and formic acid are added, even without further oxide precursors.

The calcination of the supports for the dehydrogenation catalysts used according to the present invention is advantageously carried out after application of the active components and is carried out at from 400 to 1000° C., preferably from 500 to 700° C., particularly preferably from 550 to 650° C. and in particular at from 560 to 620° C. The calcination temperature should usually be at least as high as the reaction temperature of the dehydrogenation in which the dehydrogenation catalysts are used according to the present invention.

The supports of the dehydrogenation catalysts used according to the present invention generally have high BET surface areas after calcination. The BET surface areas are generally greater than 40 $m^2/g$, preferably greater than 50 $m^2/g$, particularly preferably greater than 70 $m^2/g$. The pore volume of the dehydrogenation catalysts used according to the present invention is usually from 0.2 to 0.6 ml/g, preferably from 0.25 to 0.5 ml/g. The mean pore diameter of the dehydrogenation catalysts used according to the present invention, which can be determined by Hg porosimetry, is from 3 to 20 nm, preferably from 4 to 15 nm.

Furthermore, the dehydrogenation catalysts used according to the present invention have a bimodal pore radius distribution. The pores have sizes in the range up to 20 nm and in the range from 40 to 5000 nm. These pores all together make up at least 70% of the total pore volume of the dehydrogenation catalyst. The proportion of pores smaller than 20 nm is generally in the range from 20 to 60%, while the proportion of pores in the range from 40 to 5000 nm is generally likewise from 20 to 60%.

The dehydrogenation-active component, which is usually a metal of transition group VIII, is generally applied by impregnation with a suitable metal salt precursor. Instead of impregnation, the dehydrogenation-active component can also be applied by other methods, for example spraying the metal salt precursor onto the support. Suitable metal salt precursors are, for example, the nitrates, acetates and chlorides of the corresponding metals; complex anions of the metals used are also possible. Preference is given to using platinum as $H_2PtCl_6$ or $Pt(NO_3)_2$. Suitable solvents for the metal salt precursors include both water and organic solvents. Particularly useful solvents are water and lower alcohols such as methanol and ethanol.

When using noble metals as dehydrogenation-active components, suitable precursors also include the corresponding noble metal sols which can be prepared by one of the known methods, for example by reduction of a metal salt using a reducing agent in the presence of a stabilizer such as PVP. The method of preparation is dealt with comprehensively in the German Patent Application DE 195 00 366.

The amount of a noble metal present as dehydrogenation-active component in the dehydrogenation catalysts used according to the present invention is from 0 to 5% by weight, preferably from 0.05 to 1% by weight, particularly preferably from 0.05 to 0.5% by weight.

The further components of the active composition can be applied either during production of the support, for example by coprecipitation, or subsequently, for example by impregnating the support with suitable precursor compounds. Precursor compounds used are generally compounds which can be converted into the corresponding oxides by calcination. Suitable precursors are, for example, hydroxides, carbonates, oxalates, acetates, chlorides or mixed hydroxycarbonates of the corresponding metals.

In advantageous embodiments, the active composition further comprises the following additional components:
 at least one element of main group I or II, preferably cesium and/or potassium, in an amount of from 0 to 20% by weight, preferably from 0.1 to 15% by weight, particularly preferably from 0.2 to 10% by weight;

at least one element of transition group III including the lanthanides and actinides, preferably lanthanum and/or cerium, in an amount of from 0 to 20% by weight, preferably from 0.1 to 15% by weight, particularly preferably from 0.2 to 10% by weight;

at least one element of main groups III and IV, preferably tin, in an amount of from 0 to 10% by weight.

The dehydrogenation catalyst is preferably halogen-free.

The dehydrogenation catalyst can be used in the form of a fixed bed in the reactor or, for example, in the form of a fluidized bed and can have an appropriate shape. Suitable shapes are, for example, granules, pellets, monoliths, spheres or extrudates (rods, wagon wheels, stars, rings).

As dehydrogenatable hydrocarbons, it is possible to use paraffins, alkylaromatics, naphthenes or olefins having from 2 to 30 carbon atoms. The process is particularly useful for the dehydrogenation of straight-chain or branched hydrocarbons having a chain length of from 2 to 15 carbon atoms, preferably from 2 to 5 carbon atoms. Examples are ethane, propane, n-butane, isobutane, n-pentane, isopentane, n-hexane, n-heptane, n-octane, n-nonane, n-decane, n-undecane, ndodecane, n-tridecane, n-tetradecane and n-pentadecane. The particularly preferred hydrocarbon is propane. In the further description of the invention, the discussion will frequently concern this particularly preferred case of propane dehydrogenation, but the corresponding features apply analogously to other dehydrogenatable hydrocarbons.

Since the dehydrogenation reaction is accompanied by an increase in volume, the conversion can be increased by lowering the partial pressure of the reactants. This can be achived in a simple manner by, for example, dehydrogenation under reduced pressure and/or by mixing in an inert gas. Suitable inert gases are, for example, nitrogen, steam, carbon dioxide and noble gases such as He, Ne or Ar. Preference is given to diluents which are inert under the reaction conditions (i.e. diluents which are changed chemically to an extent of less than 5 mol %, preferably less than 3 mol % and even better less than 1 mol %). A further advantage of dilution with steam is generally reduced carbonization of the dehydrogenation catalyst used according to the present invention and thus an increased operating life, since the steam reacts with carbon formed according to the principle of carbon gasification. The ratio of steam to the hydrocarbon to be dehydrogenated is in the range from 0 to 10 mol/mol, preferably from 0.1 to 5 mol/mol.

The process of the present invention is carried out in at least one reaction zone with simultaneous generation of heat by exothermic reaction of hydrogen, hydrocarbon and/or carbon in the presence of an oxygen-containing gas. In general, the total amount of oxygen introduced, based on the total amount of the hydrocarbon to be dehydrogenated, is from 0.001 to 0.5 mol/mol, preferably from 0.005 to 0.2 mol/mol, particularly preferably from 0.05 to 0.2 mol/mol. In general, the amount of oxygen-containing gas added to the reaction gas mixture is chosen so that the combustion of the hydrogen or hydrocarbon present in the reaction gas mixture and/or the carbon present in the form of carbon deposits generates the quantity of heat required for dehydrogenation of the hydrocarbon to the alkene. In particular embodiments, the quantity of heat generated by the combustion reaction with oxygen can also be greater or lesser than the quantity of heat required for the dehydrogenation of the hydrocarbon. Oxygen can be used either as pure oxygen or in admixture with inert gases such as $CO_2$, $N_2$ or noble gases. Air is particularly preferred as oxygen-containing gas. As an alternative to molecular oxygen, it is also possible to use further oxygen-containing gaseous oxidants, for example dinitrogen oxide or ozone. The inert gases and the resulting combustion gases generally have an additional diluting effect and thus promote the heterogeneously catalyzed dehydrogenation.

The hydrogen burnt for heat generation can be the hydrogen formed in the dehydrogenation or be additional hydrogen added to the reaction gas mixture.

In one embodiment of the invention, no hydrogen is added to the reaction gas mixture and the heat required for dehydrogenation is generated at least partly by combustion (exothermic reaction) of hydrocarbon and of the hydrogen formed in the dehydrogenation.

In a further embodiment, additional hydrogen is added to the reaction gas mixture.

The dehydrogenation catalyst used according to the present invention generally also catalyzes the combustion of hydrocarbons and of hydrogen with oxygen, so that no specific oxidation catalyst different from this is necessary in principle. In one embodiment, a specific, different oxidation catalyst which selectively carbonizes the oxidation of hydrogen for the generation of heat is used in addition to the dehydrogenation catalyst, particularly when additional hydrogen is added.

If, as in one embodiment of the invention, no additional hydrogen is added to the reaction gas mixture, the heat of dehydrogenation can readily be generated by catalytic combustion of the hydrocarbons and of hydrogen formed in the dehydrogenation over the dehydrogenation catalyst. Suitable, oxygen-insensitive dehydrogenation catalysts which catalyze the combustion of hydrocarbons are the above-described Lewis-acid catalysts. Preference is given to dehydrogenation catalysts of the type described above which comprise at least one element of transition group VIII, at least one element of main groups I and/or II, at least one element of main groups III and/or IV and at least one element of transition group III including the lanthanides and actinides on zirconium oxide and/or silicon dioxide as support.

In a preferred embodiment, hydrogen is added to the reaction gas mixture for direct heat generation by combustion. In general, the amount of hydrogen added to the reaction gas mixture is such that the molar ratio of $H_2/O_2$ in the reaction gas mixture immediately after the addition is from 0.1 to 200 mol/mol, preferably from 1 to 20 mol/mol, particularly preferably from 2 to 10 mol/mol. In the case of multistage reactors, this applies to each intermediate introduction of hydrogen and oxygen.

The combustion of hydrogen occurs catalytically. In one embodiment of the invention, no specific oxidation catalyst different from the dehydrogenation catalyst is used. In a particularly preferred embodiment, the reaction is carried out in the presence of one or more oxidation catalysts which selectively catalyze the combustion reaction of hydrogen and oxygen in the presence of hydrocarbons. As a result, the combustion reaction of hydrocarbons with oxygen to give CO and $CO_2$ proceeds only to a subordinate degree, which has a significant positive effect on the achieved selectivities for the formation of alkenes. The dehydrogenation catalyst and the oxidation catalyst are preferably present in different reaction zones.

In a multistage reaction, the oxidation catalyst can be present in only one reaction zone, in a plurality of reaction zones or in all reaction zones.

The catalyst which selectively catalyzes the oxidation of hydrogen in the presence of hydrocarbons is preferably located at points at which higher oxygen partial pressures prevail than at other points of the reactor, in particular in the vicinity of the feed point for the oxygen-containing gas. Oxygen-containing gas and/or hydrogen can be fed in at one or more points on the reactor.

A preferred catalyst for the selective combustion of hydrogen comprises oxides or phosphates selected from the group consisting of the oxides and phosphates of germanium, tin, lead, arsenic, antimony and bismuth.

A further, preferred catalyst for the catalytic combustion of hydrogen comprises a noble metal of transition group VIII or I.

In heterogeneously catalyzed dehydrogenations of hydrocarbons, small amounts of high-boiling, high molecular weight organic compounds or carbon are generally formed over time, and these deposit on the catalyst surface and deactivate the catalyst as time goes on. The dehydrogenation catalysts used according to the present invention have a low tendency to suffer from carbonization and have a low deactivation rate.

The dehydrogenation catalysts used according to the present invention make it possible to achieve high space-time yields which for the dehydrogenation of propane are above 2 kg of propene/kg of catalyst*h and are thus significantly above the space-time yields of the processes of the prior art. Diluting the reaction gas mixture with inert gas, increasing the reaction temperature and/or lowering the reaction pressure enable the thermodynamically possible limiting conversions to be increased so far that they are significantly above the reaction conversions sought. In this way, space-time yields of over 6 kg of propene/kg of catalyst*h can be achieved in the presence of the catalysts used according to the present invention.

The space velocity (GHSV) over the catalyst in this operating mode also referred to as high-load operation can be >8000 $h^{-1}$.

Regeneration of the dehydrogenation catalyst can be carried out using methods known per se. Thus, as described above, steam can be added to the reaction gas mixture. The deposited carbon is partly or completely removed under these reaction conditions according to the principle of carbon gasification.

As an alternative, an oxygen-containing gas can be passed at high temperature over the catalyst bed from time to time so as to burn off the deposited carbon.

After a prolonged period of operation, the dehydrogenation catalyst used according to the present invention is preferably regenerated by, at a temperature of from 300 to 600° C., frequently at from 350 to 500° C., firstly carrying out a flushing operation with inert gas and subsequently, in a first regeneration step, passing air diluted with nitrogen over the catalyst bed. The space velocity over the catalyst is preferably from 50 to 10 000 $h^{-1}$ and the oxygen content is from about 0.5 to 2% by volume. In subsequent regeneration steps, the oxygen content is gradually increased to about 20% by volume (pure air). Preference is given to carrying out from 2 to 10, particularly preferably from 2 to 5, regeneration steps. In general, the catalyst is subsequently regenerated further using pure hydrogen or hydrogen diluted with an inert gas (hydrogen content >1% by volume) under otherwise identical conditions. All regeneration steps are preferably carried out in the presence of water vapor.

The process of the present invention can in principle be carried out in all reactor types known from the prior art and by all operating procedures known from the prior art. The additional introduction of oxygen leads to at least part of the heat of reaction or of the energy required for heating the reaction gas mixture being supplied by direct combustion and not having to be introduced indirectly via heat exchangers.

A comprehensive description of suitable reactor types and operating procedures is also given in "Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.".

A suitable form of reactor is a fixed-bed tube or multitube (shell-and-tube) reactor. In this, the catalyst (dehydrogenation catalyst and, if desired, specific oxidation catalyst) is present as a fixed bed in a reaction tube or in a bundle of reaction tubes. The reaction tubes are customarily heated indirectly by a gas, e.g. a hydrocarbon such as methane, being burnt in the space surrounding the reaction tubes. In such a reactor, it is advantageous to employ this indirect form of heating only for the first about 20–30% of the length of the fixed bed and to heat the remaining length of the bed to the required reaction temperature by means of the radiative heat liberated by the indirect heating. According to the present invention, the indirect heating of the reaction gas can advantageously be coupled with the direct heating by combustion in the reaction gas mixture. Coupling the direct introduction of heat with the indirect introduction of heat makes it possible to achieve approximately isothermal reaction conditions. Customary internal diameters of the reaction tubes are from about 10 to 15 cm. A typical shell-and-tube reactor used for dehydrogenation has from about 300 to 1000 reaction tubes. The temperature in the interior of the reaction tube is generally in the range from 300 to 700° C., preferably from 400 to 700° C. The operating pressure is usually from 0.5 to 8 bar, frequently from 1 to 2 bar when using low steam dilution (corresponding to the BASF Linde process) but also from 3 to 8 bar when using a high steam dilution (corresponding to the steam active reforming process (STAR process) of Phillips Petroleum Co., cf. U.S. Pat. No. 4,902,849, U.S. Pat. No. 4,996,387 and U.S. Pat. No. 5,389,342). In general, the product mixture leaves the reaction tube at a from 50 to 100° C. lower temperature. Typical space velocities over the catalyst in the case of propane are from 500 to 2000 $h^{-1}$. The catalyst geometry can be, for example, spherical or cylindrical (hollow or solid).

The process of the present invention can also be carried out in a moving bed reactor. For example, the moving catalyst bed can be accommodated in a radial flow reactor. In this, the catalyst slowly moves from the top downward, while the reaction gas mixture flows radially. This method of operation is employed, for example, in the UOP-Oleflex dehydrogenation process. Since the reactors are operated pseudoadiabatically in this process, it is advantageous to employ a plurality of reactors connected in series (typically up to four reactors). Before or in each reactor, the inflowing gas mixture is heated to the required reaction temperature by combustion in the presence of the oxygen fed in. The use of a plurality of reactors makes it possible to avoid large differences in the temperatures of the reaction gas mixture between reactor inlet and reactor outlet while nevertheless achieving high total conversions.

When the catalyst has left the moving bed reactor, it is passed to regeneration and subsequently reused. The dehydrogenation catalyst used according to the present invention generally has a spherical shape. Hydrogen can also be added to the hydrocarbon to be dehydrogenated, preferably propane, to avoid rapid catalyst deactivation. The operating pressure is typically from 2 to 5 bar. The molar ratio of hydrogen to propane is preferably from 0.1 to 10. The reaction temperatures are preferably from 550 to 660° C.

A hydrocarbon dehydrogenation by the process of the present invention can also, as described in Chem. Eng. Sci.

1992 b, 47 (9–11) 2313, be carried out in the presence of a heterogeneous catalyst in a fluidized bed, with the hydrocarbon not being diluted. In this method, two fluidized beds are advantageously operated in parallel, with one of them generally being in the regeneration mode. The operating pressure is typically from 1 to 2 bar, and the dehydrogenation temperature is generally from 550 to 600° C. The heat necessary for the dehydrogenation is introduced into the reaction system by preheating the dehydrogenation catalyst to the reaction temperature. The use according to the present invention of an oxygen-containing co-feed makes it possible to omit the preheater and to generate the necessary heat directly in the reactor system by combustion in the presence of oxygen.

In a particularly preferred embodiment of the process of the present invention, the dehydrogenation is carried out in a tray reactor. This contains one or more successive catalyst beds. The number of catalyst beds can be from 1 to 20, advantageously from 2 to 8, in particular from 4 to 6. The reaction gas preferably flows radially or axially through the catalyst beds. In general, such a tray reactor is operated using a fixed catalyst bed.

In the simplest case, the fixed catalyst beds are arranged axially or in the annular gaps of concentric, upright mesh cylinders in a shaft furnace reactor. One shaft furnace reactor corresponds to one tray. It is possible for the process of the present invention to be carried out in a single shaft furnace reactor, but this is less preferred.

In an operating mode without oxygen as co-feed, the reaction gas mixture is subjected to intermediate heating on its way from one catalyst bed to the next catalyst bed in the tray reactor, e.g. by passing it over heat exchanger ribs heated by means of hot gases or by passing it through tubes heated by means of hot combustion gases.

In the process of the present invention, the above-described intermediate heating is carried out at least partly by direct means. For this purpose, a limited amount of molecular oxygen is added to the reaction gas mixture either before it flows through the first catalyst bed and/or between the subsequent catalyst beds. Thus, hydrocarbons present in the reaction gas mixture, carbon or carbon-like compounds which have deposited on the catalyst surface and also hydrogen formed during the dehydrogenation are burnt to a limited extent over the catalyst used according to the present invention. The heat of reaction liberated in this combustion thus makes it possible for the heterogeneously catalyzed hydrocarbon dehydrogenation to be operated virtually isothermally. The process can be operated with or without introduction of additional hydrogen.

In one embodiment of the invention, intermediate introduction of oxygen-containing gas and possibly hydrogen is carried out upstream of each tray of the tray reactor. In a further embodiment of the process of the present invention, the introduction of oxygen-containing gas and possibly hydrogen is carried out upstream of each tray apart from the first tray. In a preferred embodiment, intermediate introduction of hydrogen is employed; in a specific embodiment of this, a bed of a specific oxidation catalyst is present downstream of each introduction point and is followed by a bed of the dehydrogenation catalyst, and in a second specific embodiment, no specific oxidation catalyst is present. In a further preferred embodiment, no hydrogen is introduced.

The dehydrogenation temperature is generally from 400 to 800° C. and the pressure is generally from 0.2 to 5 bar, preferably from 0.5 to 2 bar, particularly preferably from 1 to 1.5 bar. The space velocity (GHSV) is generally from 500 to 2000 $h^{-1}$ and in high-load operation up to 16000 $h^{-1}$, preferably from 4000 to 16000 $h^{-1}$.

The hydrocarbon used in the process of the present invention does not have to be a pure compound. Rather, the hydrocarbon used can comprise other dehydrogenatable gases such as methane, ethane, ethylene, propane, propene, butanes, butenes, propyne, acetylene, $H_2S$ or pentanes. In particular, the dehydrogenation of the present invention can also be carried out using alkane mixtures which are produced industrially and are available in large quantities, for example LPG (liquefied petroleum gas). It is also possible to use circulation gases originating from other processes, for example as described in the German Patent Application P 10028582.1.

The output from the reactor is worked up in a manner known per se, for example by separating off the molecular hydrogen present in the product mixture, separating off constituents other than alkanes and alkenes, preferably by selective absorption of the alkene/alkane mixture in an organic solvent, and fractionation of the alkene/alkane mixture in a $C_3$ splitter and recirculation of the alkane to the dehydrogenation.

The invention is illustrated by the following examples.

EXAMPLES

Example 1

A solution of 11.992 g of $SnCl_2.2H_2O$ and 7.888 g of $H_2PtCl_6.6H_2O$ in 5950 ml of ethanol was poured over 1000 g of a granulated $ZrO_2.SiO_2$ mixed oxide from Norton (screen fraction: 1.6 to 2 mm).

The supernatant ethanol was taken off on a rotary evaporator. The mixed oxide granules were subsequently dried at 100° C. for 15 hours and calcined at 560° C. for 3 hours. A solution of 7.68 g of $CsNO_3$, 13.54 g of $KNO_3$ and 98.329 g of $La(NO_3)_3.6H_2O$ in 23 ml of $H_2O$ was then poured over the catalyst obtained. The supernatant water was taken off on a rotary evaporator. The material was subsequently dried at 100° C. for 15 hours and calcined at 560° C. for 3 hours.

The catalyst had a BET surface area of 85 $m^2/g$. Mercury porosimetry measurements indicated a pore volume of 0.29 ml/g.

Example 2

A solution of 0.6 g of $SnCl_2.2H_2O$ and 0.394 g of $H_2PtCl_6.6H_2O$ in 300 ml of ethanol was poured over 55 g of a granulated $ZrO_2.SiO_2$ mixed oxide from Norton (screen fraction: 1.6 to 2 mm).

The supernatant ethanol was taken off on a rotary evaporator. The mixed oxide granules were subsequently dried at 100° C. for 15 hours and calcined at 560° C. for 3 hours. A solution of 0.386 g of $CsNO_3$, 0.680 g of $KNO_3$ and 4.888 g of $Ce(NO_3)_3.6H_2O$ in 130 ml of $H_2O$ was then poured over the catalyst. The supernatant water was taken off on a rotary evaporator. The material was subsequently dried at 1 00° C. for 15 hours and calcined at 560° C. for 3 hours.

The catalyst had a BET surface area of 72.4 $m^2/g$. Mercury porosimetry measurements indicated a pore volume of 0.26 ml/g.

Example 3

A solution of 0.684 g of $SnCl_2.2H_2O$ and 0.45 g of $H_2PtCl_6.6H_2O$ in 342 ml of ethanol was poured over 57 g of a granulated $ZrO_2$ support from Norton (screen fraction: 1.6 to 2 mm).

The supernatant ethanol was taken off on a rotary evaporator. The mixed oxide granules were subsequently dried at 100° C. for 15 hours and calcined at 560° C. for 3 hours. A solution of 0.44 g of CsNO$_3$, 0.775 g of KNO$_3$ and 5.604 g of Ce(NO$_3$)$_3$.6H$_2$O in 148 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 40 m$^2$/g. Mercury porosimetry measurements indicated a pore volume of 0.25 ml/g.

Example 4

In a 5 l stirred flask, 521.3 g of Zr(OH)$_4$ were suspended in 2000 ml of H2O. 73.53 g of SiO$_2$ Ludox sol (SiO$_2$ content: 47.6% by weight) were added to the suspension. The suspension was stirred at room temperature for 4 hours. The product was subsequently spray dried. The temperature at the top was set to 350° C., the outlet temperature was from 105 to 110° C., and the spraying pressure was 2.5 bar. The atomizer disk rotated at a speed of 28 000 rpm. The resulting white powder had a loss on ignition of 15.1%.

471.15 g of the white powder were kneaded with 133.30 g of Pural SCF (Al$_2$O$_3$) and 30.22 g of concentrated HNO$_3$ for 2 hours. The paste was shaped to form 3 mm extrudates by means of a ram extruder (pressing pressure: 75 bar). The extrudates were dried at 200° C. for 4 hours and calcined at 600° C. for 2 hours. The extrudates were subsequently crushed to give particles of a screen fraction from 1.6 to 2 mm.

A solution of 0.712 g of SnCl$_2$.2H$_2$O and 0.468 g of H$_2$PtCl$_6$.6H$_2$O in 368 ml of ethanol was poured over 60 g of the support produced in this way.

The supernatant ethanol was taken off on a rotary evaporator. The mixed oxide granules were subsequently dried at 100° C. for 15 hours and calcined at 560° C. for 3 hours. A solution of 0.458 g of CsNO$_3$, 0.807 g of KNO$_3$ and 5.838 g of La(NO$_3$)$_3$.6H$_2$O in 157 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 98 m$^2$/g. Mercury porosimetry measurements indicated a pore volume of 0.35 ml/g.

Example 5

23 g of a granulated Mg(Al)O support from Giulini (screen fraction: 1.6 to 2 mm) were calcined at 700° C. for 2 hours. A solution of 0.276 g of SnCl$_2$.2H$_2$O and 0.181 g of H$_2$PtCl$_6$.6H$_2$O in 138 ml of ethanol was subsequently poured over the support.

The supernatant ethanol was taken off on a rotary evaporator. The mixed oxide granules were subsequently dried at 100° C. for 15 hours and calcined at 560° C. for 3 hours. A solution of 0.177 g of CsNO$_3$, 0.313 g of KNO$_3$ and 2.262 g of La(NO$_3$)$_3$.6H$_2$O in 60 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 103 m$^2$/g. Mercury porosimetry measurements indicated a pore volume of 0.51 ml/g.

Example 6

A solution of 0.3718 g of SnCl$_2$.2H$_2$O and 0.245 g of H$_2$PtCl$_6$.6H$_2$O in 190 ml of ethanol was poured over 57 g of a granulated theta-Al$_2$O$_3$ support from Condea (screen fraction: 1.6 to 2 mm).

The supernatant ethanol was taken off on a rotary evaporator. The mixed oxide granules were subsequently dried at 100° C. for 15 hours and calcined at 560° C. for 3 hours. A solution of 0.239 g of CsNO$_3$, 0.4214 g of KNO$_3$ and 5.604 g of La(NO$_3$)$_3$.6H$_2$O in 80 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 119 m$^2$/g. Mercury porosimetry measurements indicated a pore volume of 0.66 ml/g.

Example 7

A solution of 0.2758 g of SnCl$_2$.2H$_2$O and 0.1814 g of H$_2$PtCl$_6$.6H$_2$O in 138 ml of ethanol was poured over 23 g of a granulated theta-Al$_2$O$_3$ support from BASF (screen fraction: 1.6 to 2 mm).

The supernatant ethanol was taken off on a rotary evaporator. The mixed oxide granules were subsequently dried at 100° C. for 15 hours and calcined at 560° C. for 3 hours. A solution of 0.1773 g of CsNO$_3$, 0.3127 g of KNO$_3$ and 2.26 g of La(NO$_3$)$_3$.6H$_2$O in 60 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 34 m$^2$/g. Mercury porosimetry measurements indicated a pore volume of 0.23 ml/g.

Example 8

43.25 g of (NH$_4$)$_2$CO$_3$ were dissolved in 1 l of water, mixed with 849 ml of a 25% strength by weight ammonia solution and heated to 75° C. 2333.3 g of Mg(NO$_3$)$_2$.6H$_2$O and 337.6 g of Al(NO$_3$)$_3$.9H$_2$O dissolved in 3 l of water were added quickly to the solution from a dropping funnel while stirring. After the mixture had been stirred at 75° C. for 1 hour, the resulting precipitate was filtered off and the filter cake was washed with water. The solid was subsequently dried at 100° C. for hours and calcined at 900° C. for 2 hours.

The powder was mixed with 3% by weight of magnesium stearate and precompacted to form 20×2 mm tablets on an eccentric press.

33 g of the Mg(Al)O support produced in this way were crushed (screen fraction: 1.6 to 2 mm) and calcined at 700° C. for 2 hours. A solution of 0.398 g of SnCl$_2$.2H$_2$O and 0.262 g of H$_2$PtCl$_6$.6H$_2$O in 200 ml of ethanol was subsequently poured over the support.

The supernatant ethanol was taken off on a rotary evaporator. The mixed oxide granules were subsequently dried at 100° C. for 15 hours and calcined at 560° C. for 3 hours. A solution of 0.256 g of CsNO$_3$, 0.451 g of KNO$_3$ and 3.265 g of La(NO$_3$)$_3$.6H$_2$O in 87 ml of H$_2$O was then poured over the catalyst. The supernatant water was taken off on a rotary evaporator. The material was subsequently dried at 100° C. for 15 hours and calcined at 560° C. for 3 hours.

The catalyst had a BET surface area of 85 m$^2$/g. Mercury porosimetry measurements indicated a pore volume of 0.28 ml/g.

Example 9

Catalyst Test:

20 ml of the previously produced catalyst were installed in a tube reactor having an internal diameter of 20 mm. The catalyst was treated with hydrogen for 30 minutes at 500° C.

The catalyst was then exposed to a mixture of 80% by volume of nitrogen and 20% by volume of air (lean air) at the same temperature. After a flushing phase of 15 minutes using pure nitrogen, the catalyst was reduced by means of hydrogen for 30 minutes. The catalyst was then supplied with 20 standard l/h of propane (99.5% by volume) and $H_2O$ in a molar ratio of propane/water vapor of 1:1 at a reaction temperature of 610° C. The pressure was 1.5 bar and the space velocity (GHSV) was 2000 $h^{-1}$. The reaction products were analyzed by gas chromatography. The results are summarized in the table.

The Brönsted and Lewis acidities of the catalysts produced in Examples 1 to 8 were determined by means of the probe gas pyridine using an HV-FTIR measurement cell.

The samples were baked in air at 390° C. for 1 hour, subsequently evacuated to $10^{-5}$ mbar, cooled to 80° C. and treated with gaseous pyridine at an equilibrium pressure of 3 mbar. To test the evacuation stability of the pyridine adsorbate, the sample which had been treated with gaseous pyridine at 3 mbar was subjected to a vacuum treatment in an oil pump vacuum (about $10^{-2}$ mbar, 3 min) and under high vacuum (about $10^{-5}$ mbar, 1 h). Physisorbate material was thus desorbed. The adsorbate spectra were recorded in a high vacuum.

The measured absorbances were expressed as a ratio to the thickness of the sample (in integrated extinction units (IEE) per µm of thickness). The single-beam spectrum of the sample which had not been treated with pyridine gas and had been cooled to 80° C. under high vacuum served as background for the adsorbate spectra. Matrix bands were thus completely balanced out.

The band at 1440 $cm^{-1}$ (corresponds to Lewis-acid centers) and additionally the control band at 1490 $cm^{-1}$ (corresponds to Lewis-acid centers if no Brönsted-acid centers are present) were evaluated.

The results are summarized in the table.

All samples examined displayed no measurable Brönsted acidity. The measured Lewis acidity correlates well with the conversion in the dehydrogenation of propane.

TABLE

| Example | Support | Lewis acidity (AU) | Propane conversion (%) |
|---|---|---|---|
| 1 | $ZrO_2/SiO_2$ (Norton) | 8.97 | 46.8 |
| 2 | $ZrO_2/SiO_2$ (Ce instead of La) | 7.82 | 47.2 |
| 3 | $ZrO_2$ (Norton) | 4.59 | 30 |
| 4 | $ZrO_2/SiO_2/Al_2O_3$ | 7.29 | 42.1 |
| 5 | Mg(Al)O (Giulini) | 2.88 | 12.4 |
| 6 | theta-$Al_2O_3$ (Condea) | 3.51 | 30.4 |
| 7 | theta-$Al_2O_3$ (BASF) | 1.77 | 11.4 |
| 8 | Mg(Al)O | 1.66 | 12.2 |

All supports are loaded with $Pt_{0.3}/Sn_{0.6}/Cs_{0.5}/K_{0.5}/La_{3.0}$.

Example 10

High-load Operation 2.5 ml of the catalyst produced as described in Example 1 were diluted with 77.5 ml of steatite and installed in a tube reactor having an internal diameter of 20 mm. The catalyst was treated in succession, for 30 minutes each at 500° C., firstly with hydrogen, then with lean air (80% by volume of nitrogen and 20% by volume of air) and subsequently again with hydrogen. The catalyst was flushed with nitrogen for 15 minutes between each of the treatments. The catalyst was subsequently supplied at 600° C. with 20 standard l/h of propane (99.5% by volume) and water vapor in a molar ratio of propane/$H_2O$ of 1:1. The pressure was 1.5 bar and the space velocity (GHSV) was 16 000 $h^-$. The reaction products were analyzed by gas chromatography. After a reaction time of one hour, 30% of the input propane were converted at a selectivity to propene of 95%. The space-time yield of propene, based on the catalyst volume used, was 8 g of propene/(g of catalyst*h).

Example 11

Operation with Oxygen 20 ml of the catalyst produced as described in Example 1 were installed in a tube reactor having an internal diameter of 20 mm. The catalyst was treated in succession, for 30 minutes each at 500° C., firstly with hydrogen, then with lean air (80% by volume of nitrogen and 20% by volume of air) and subsequently again with hydrogen. The catalyst was flushed with nitrogen for 15 minutes between each of the treatments. The catalyst was subsequently supplied at 610° C. with 20 standard l/h of propane (99.5% by volume) and water vapor in a molar ratio of propane/$H_2O$ of 1:1. In addition, oxygen was introduced in a molar ratio of propane/$O_2$ of 20:1. The pressure was 1.5 bar and the space velocity (GHSV) was 2100 $h^{-1}$. The reaction products were analyzed by gas chromatography. After a reaction time of one hour, 50% of the input propane were converted at a selectivity to propene of 90%. After a reaction time of 16 hours, the conversion was 44% and the selectivity was 90%.

Example 12

Operation with Oxygen at Low Conversion 20 ml of the catalyst produced as described in Example 1 were installed in a tube reactor having an internal diameter of 20 mm. The catalyst was treated in succession, for 30 minutes each at 500° C., firstly with hydrogen, then with lean air (80% by volume of nitrogen and 20% by volume of air) and subsequently again with hydrogen. The catalyst was flushed with nitrogen for 15 minutes between each of the treatments. The catalyst was subsequently supplied at 500° C. with 20 standard l/h of propane (99.5% by volume) and water vapor in a molar ratio of propane/$H_2O$ of 1:1. In addition, oxygen was introduced in a molar ratio of propane/$O_2$ of 20:1. The pressure was 1.5 bar and the space velocity (GHSV) was 2100 $h^{-1}$. The reaction products were analyzed by gas chromatography. After a reaction time of one hour, 16% of the input propane were converted at a selectivity to propene of 99%. After a reaction time of 100 hours, the conversion was 14% and the selectivity was 94%. After increasing the temperature to 510° C., the propane conversion after 300 hours was 15% and the selectivity was 94%. After increasing the temperature further to 530° C., 15% of the input propane were being converted at a selectivity to propene of 94% after 800 hours. After 1700 hours, the supply of propane and of water was stopped and lean air (80% by volume of nitrogen and 20% by volume of air) was passed over the catalyst at 400° C. Pure air was then passed over the catalyst for 30 minutes. After the reactor had been flushed with nitrogen for 15 minutes, hydrogen was passed over the catalyst for 30 minutes. After propane, water vapor and oxygen were again supplied as feed, a propane conversion of 15% at a selectivity of 92% could be achieved at 505° C. After a total of 2300 hours, the propane conversion at 540° C. was 15% and the selectivity to propene was 94%.

Example 13

Operation with Oxygen at Low Conversion Using Additional $N_2$ Dilution

After 2300 hours, the catalyst from Example 1 was again (after stopping propane and water vapor supply) treated with lean air (80% by volume of nitrogen and 20% by volume of air) at 400° C. Subsequently, pure air was passed over the catalyst for 30 minutes. After the reactor had been flushed with nitrogen for 15 minutes, hydrogen was passed over the catalyst for 30 minutes. Subsequently, propane, nitrogen, oxygen and water vapor in a ratio of 5.8/7.8/0.4/5.8 were passed over the catalyst at 505° C. The reaction pressure was 1.5 bar and the space velocity (GHSV) was 1300 $h^{-1}$. The propane conversion was 20% at a selectivity of 92%. After 500 hours, 20% of the propane were converted at a selectivity to propene of 92%.

Example 14
Operation with Oxygen at Low Conversion Using Additional $N_2$ Dilution and Additional Introduction of $H_2$ Using the experimental procedure of Example 12, hydrogen was additionally mixed into the feed after a total running time of 2500 hours. The feed then had the following composition: $C3/N_2/O_2/H_2/H_2O=5.8/7.8/0.4/0.8/5.8$. The reaction pressure was 1.5 bar and the space velocity (GHSV) was 1300 $h^{-1}$. The reaction temperature was set to 575° C. The propane conversion was 20% at a propene selectivity of 92%. The oxygen introduced was reacted completely. 60% of the oxygen introduced reacted with propane or propene to form carbon dioxide and carbon monoxide, 40% of the oxygen introduced reacted with hydrogen which had been introduced or formed in the dehydrogenation to give water.

Example 15
Regeneration of the Catalyst 1000 ml of the catalyst produced as described in Example 6 were diluted with 500 ml of steatite and installed in a tube reactor having an internal diameter of 40 mm. The catalyst was treated in succession, for 30 minutes each at 500° C., firstly with hydrogen, then with lean air (80% by volume of nitrogen and 20% by volume of air) and subsequently again with hydrogen. The catalyst was flushed with nitrogen for 15 minutes between each of the treatments. The catalyst was subsequently supplied at 610° C. with 250 standard l/h of propane (99.5% by volume) and water vapor in a molar ratio of propane/$H_2O$ of 1:1. The pressure was 1.5 bar and the space velocity (GHSV) was 500 $h^{-1}$. The reaction products were analyzed by gas chromatography. After a reaction time of one hour, 55% of the input propane were converted at a selectivity to propene of 90%. After a reaction time of 12 hours, the conversion was 53% and the selectivity was 93%. The supply of propane and water was stopped and lean air (92% by volume of nitrogen and 8% by volume of air) was passed over the catalyst at 400° C. The air content was subsequently increased twice (firstly to 83% by volume of nitrogen and 17% by volume of air, then to 64% by volume of nitrogen and 36% by volume of air). Pure air was then passed over the catalyst until the $CO_2$ content of the output gas was less than 0.04% by volume. After the reactor had been flushed with nitrogen for 15 minutes, hydrogen was passed over the catalyst for 30 minutes. After propane, water vapor and oxygen were again supplied as feed, a propane conversion of 55% at a selectivity of 92% could be achieved at 610° C. After the catalyst had been regenerated 10 times in the above-described manner, a conversion of 54% at a propene selectivity of 93% could be achieved at 610° C. After the catalyst had been regenerated 30 times, a conversion of 54% at a propene selectivity of 93% could be achieved at 610° C.

We claim:

1. A process for the heterogeneously catalyzed dehydrogenation in one or more reaction zones of one or more dehydrogenatable $C_2$–$C_{30}$-hydrocarbons in a reaction gas mixture comprising them, with at least part of the heat of dehydrogenation required being generated directly in the reaction gas mixture in at least one reaction zone by combustion of hydrogen, the hydrocarbon or hydrocarbons and/or carbon in the presence of an oxygen-containing gas, wherein the reaction gas mixture comprising the dehydrogenatable hydrocarbon or hydrocarbons is brought into contact with a Lewis-acid dehydrogenation catalyst which has essentially no Bronsted acidity, wherein the dehydrogenation catalyst has a Lewis acidity of greater than 3 acidity units (AU), determinable from IR absorption spectra of pyridine adsorbed on the catalyst.

2. A process as claimed in claim 1, wherein the dehydrogenation catalyst comprises a metal oxide selected from the group consisting of zirconium dioxide, aluminum oxide, silicon dioxide, titanium dioxide, magnesium oxide, lanthanum oxide and cerium oxide.

3. A process as claimed in claim 2, wherein the dehydrogenation catalyst comprises zirconium dioxide and/or silicon dioxide.

4. A process as claimed in any of claim 1, wherein the dehydrogenation catalyst comprises at least one element of transition group VIII, at least one element of main group I or II, at least one element of main group III or IV and at least one element of transition group III including the lanthanides and actinides.

5. A process as claimed in any of claim 1, wherein the dehydrogenation catalyst comprises platinum and/or palladium.

6. A process as claimed in any of claim 1, wherein the dehydrogenation catalyst comprises cesium and/or potassium.

7. A process as claimed in any of claim 1, wherein the dehydrogenation catalyst comprises lanthanum and/or cerium.

8. A process as claimed in any of claim 1, wherein the dehydrogenation catalyst comprises tin.

9. A process as claimed in any of claim 1, wherein the dehydrogenation catalyst has a bimodal pore radius distribution in which from 70% to 100% of the pores have a pore diameter less than 20 nm or in the range from 40 to 5000 nm.

10. A process as claimed in any of claim 1, wherein the reaction gas mixture comprises water vapor.

11. A process as claimed in any of claim 1, wherein hydrogen is added to the reaction gas mixture.

12. A process as claimed in claim 11, wherein at least one reaction zone contains a catalyst which selectively catalyzes the combustion reaction of hydrogen and oxygen in the presence of hydrocarbons.

13. A process as claimed in any of claim 1, wherein the catalyst which catalyzes the combustion of hydrogen comprises oxides or phosphates selected from the group consisting of the oxides and phosphates of germanium, tin, lead, arsenic, antimony and bismuth.

14. A process as claimed in claim 1, wherein the catalyst which which selectively catalyzes the combustion of hydrogen comprises a noble metal of transition group VIII or I.

15. A process as claimed in claim 1, wherein the dehydrogenation is carried out in a tray reactor.

16. A process as claimed in claim 1, wherein the dehydrogenation catalyst has a Lewis acidity of greater than 6 acidity units (AU), determinable from IR absorption spectra of pyridine adsorbed on the catalyst.

17. A process as claimed in claim 16, wherein the dehydrogenation catalyst comprises a metal oxide selected form the group consisting of zirconium dioxide, aluminium oxide, silicon dioxide, titanium dioxide, magnesium oxide, lanthanum oxide and cerium oxide.

18. A process as claimed in claim 17, wherein the dehydrogenation catalyst comprises zirconium dioxide and silicon dioxide.

* * * * *